United States Patent
Markham et al.

(10) Patent No.: US 8,940,085 B2
(45) Date of Patent: Jan. 27, 2015

(54) HUMIDIFIER WITH ULTRAVIOLET DISINFECTION

(75) Inventors: Ronald C. Markham, Ada, MI (US); Matthew J. Barton, Farmington Hills, MI (US)

(73) Assignee: Access Business Group International LLC, Ada, MI (US)

( * ) Notice: Subject to any disclaimer, the term of this patent is extended or adjusted under 35 U.S.C. 154(b) by 324 days.

(21) Appl. No.: 13/421,074

(22) Filed: Mar. 15, 2012

(65) Prior Publication Data

US 2012/0234166 A1    Sep. 20, 2012

Related U.S. Application Data

(60) Provisional application No. 61/453,157, filed on Mar. 16, 2011.

(51) Int. Cl.
*B01F 3/04* (2006.01)

(52) U.S. Cl.
USPC ............... 96/224; 261/30; 261/78.2; 261/81; 261/107; 261/119.1; 261/DIG. 65

(58) Field of Classification Search
CPC ...... B01F 3/04; B01F 3/04021; B01F 3/0407; B01F 3/022
USPC .......... 261/30, 81, 78.2, 107, 119.1, DIG. 65; 96/224; 210/263
See application file for complete search history.

(56) References Cited

U.S. PATENT DOCUMENTS

| | | | |
|---|---|---|---|
| 5,677,982 A | 10/1997 | Levine et al. | |
| 6,220,579 B1 | 4/2001 | Chen | |
| 6,825,620 B2 | 11/2004 | Kuennen et al. | |
| 6,845,971 B2 | 1/2005 | Bachert | |
| 7,212,414 B2 | 5/2007 | Baarman | |
| 7,522,878 B2 | 4/2009 | Baarman | |
| 2010/0133162 A1 | 6/2010 | Huang | |
| 2010/0133707 A1* | 6/2010 | Huang | 261/81 |

FOREIGN PATENT DOCUMENTS

| | | | |
|---|---|---|---|
| DE | 88 00 625 | | 4/1988 |
| JP | 2007051826 A | * | 3/2007 |

(Continued)

OTHER PUBLICATIONS

PDF document Quartz or Glass?, LOT Oriel Group.*
PDF Document Quartz or Glass? , LOT Oriel Group, Date Not Available.*
International Search Report, Application No. PCT/US2012/029207, mailed Jul. 30, 2012.

(Continued)

*Primary Examiner* — Robert A Hopkins
(74) *Attorney, Agent, or Firm* — Warner Norcross & Judd LLP

(57) ABSTRACT

A humidifier for treating humidified air with germicidal light is provided. The humidifier includes a water reservoir, an atomizer to atomize a supply of water, and an ultraviolet light source to expose the atomized water to germicidal light. The ultraviolet light source extends vertically within a cylindrical channel to irradiate the atomized water dissipating upwardly from the atomizer. The water reservoir can include a carbon filter and a hardness-removing module for removing containments and metal oxides from the water supply. A control panel indicates the remaining useful life of the ultraviolet light source, the carbon filter and the hardness-removing module based on historical humidifier usage and water quality levels.

18 Claims, 3 Drawing Sheets

(56) References Cited

FOREIGN PATENT DOCUMENTS

WO 2008/002123 1/2008
WO WO2010/027282 3/2010

OTHER PUBLICATIONS

Written Opinion of the International Searching Authority, Application No. PCT/US2012/029207, mailed Jul. 30, 2012.

* cited by examiner

HUMIDIFIER WITH ULTRAVIOLET DISINFECTION

BACKGROUND OF THE INVENTION

The invention pertains to humidifiers, and more particularly, to humidifiers having an internal ultraviolet light source.

Humidifiers are commonly used to increase the relative humidity within an enclosed space. The increase in humidity can be desirable for a number of reasons. For example, relative humidity levels greater than 25% can minimize discomfort in the skin, eyes, nose or throat while also minimizing the risk of electric shock. In addition, humidifiers can be particularly desirable during winter months when heated inside air can cause the relative humidity to fall to uncomfortable levels.

Various types of humidifiers are used to increase relative humidity. Exemplary humidifiers can include evaporative humidifiers, steam vaporizing humidifiers, and ultrasonic humidifiers. Evaporative humidifiers increase relative humidity by directing dry air against a wick that is saturated with water. Steam vaporizing humidifiers typically include an electric heating element submerged within a water reservoir for creating steam. In addition, ultrasonic humidifiers typically include an ultrasonic transducer to atomize water with high frequency vibrations.

Each category of humidifier will generally include an internal water reservoir. In many instances, however, the water reservoir can become home to bacteria or mold, particularly after repeated uses. As the humidifier circulates humidified air into the ambient environment, it may also circulate bacteria and mold. This can result in discomfort for allergy sufferers, and can increase the risk of colds and other ailments.

To reduce the presence of bacteria and mold in the water reservoir, some existing humidifiers include an ultraviolet lamp to sterilize the water within the water reservoir. However, microorganisms can accumulate downstream of the water reservoir, generally free from the effects of the ultraviolet lamp. Also, solid contaminants from within the water supply can build up over time within the reservoir and in other portions of the humidifier. Ultimately, these microorganisms and contaminants can mix with the humidified air stream and can circulate into the ambient environment.

Accordingly, there remains a continued need for an improved humidifier for providing a sterilized output. In addition, there remains a continued need for an improved humidifier for leveraging the benefits of ultraviolet light in conjunction with point-of-use humidifiers and forced air humidifiers.

SUMMARY OF THE INVENTION

A system and a method for humidifying air are provided. The system includes an atomizer and an ultraviolet light source. The atomizer increases the moisture content of a volume of air, and the ultraviolet light sources exposes the resulting humidified air with germicidal light prior to dispersal of the humidified air into the ambient environment.

In one embodiment, the system includes a point-of-use humidifier and base station. The humidifier includes a water reservoir, an ultrasonic nebulizer, and an ultraviolet lamp. The reservoir provides a regulated supply of water to the ultrasonic nebulizer. The ultrasonic nebulizer is seated below the water reservoir and converts the supply of water into an atomized mist. The mist mixes with the untreated air and flows upwardly along the ultraviolet lamp. The ultraviolet lamp treats the passing air and water mixture with ultraviolet radiation prior to its discharge into the ambient environment.

In another embodiment, the base station includes a blower. The blower directs untreated ambient air from the exterior of the humidifier system to within the humidifier and upwardly along the ultraviolet lamp. The ultraviolet lamp can operate independently or cooperatively with the atomizer to sterilize dry air or humidified air, respectively. In addition, the water reservoir can be toroidally shaped, and the ultraviolet lamp can extend generally vertically through a core of the water reservoir.

In yet another embodiment, the water reservoir includes a carbon block filter and a hardness removal unit. The carbon block filter and the hardness removal unit are serially connected between a reservoir inlet and a reservoir outlet. The carbon block filter and the hardness removal unit operate to remove suspended solids and metal oxides from the water supply. A control panel can alert a user to replace either or both of the carbon block filter and the hardness removal unit after repeated uses.

In still another embodiment, an ultraviolet lamp provides UV-C radiation having a wavelength of between 100 and 280 nanometers. The ultraviolet lamp is positioned within an elongate channel having an interior surface that is reflective to ultraviolet light. The interior surface is spaced apart from the ultraviolet lamp to permit the circulation of humidified air in a direction generally parallel to the lamp outer surface.

In another embodiment, a method for humidifying air includes providing a fluid flow path in communication with the ambient environment, increasing the moisture content of ambient air circulating through the fluid flow path, exposing the resulting humidified air to ultraviolet light, and discharging the humidified air from the fluid flow path into the ambient environment. The method can additionally include filtering ambient air circulating through the fluid flow path. The fluid flow path is optionally defined by a cylindrical sidewall spaced apart from an ultraviolet light source.

Embodiments of the invention can therefore provide an improved system and method for dispersing sterilized humidified air. By atomizing the water before sterilization, the discharged air is generally free of viable microorganisms from the water supply and from the untreated air. In addition, the application of one or more filters can prevent the dispersal of solid contaminants into the surrounding environment and can reduce the presence of suspended solids in the humidified air, which could otherwise impede the effectiveness of the ultraviolet lamp.

These and other advantages and features of the invention will be more fully understood and appreciated by reference to the description of the current embodiments and the drawings.

DESCRIPTION OF THE CURRENT EMBODIMENTS

Figure 1:
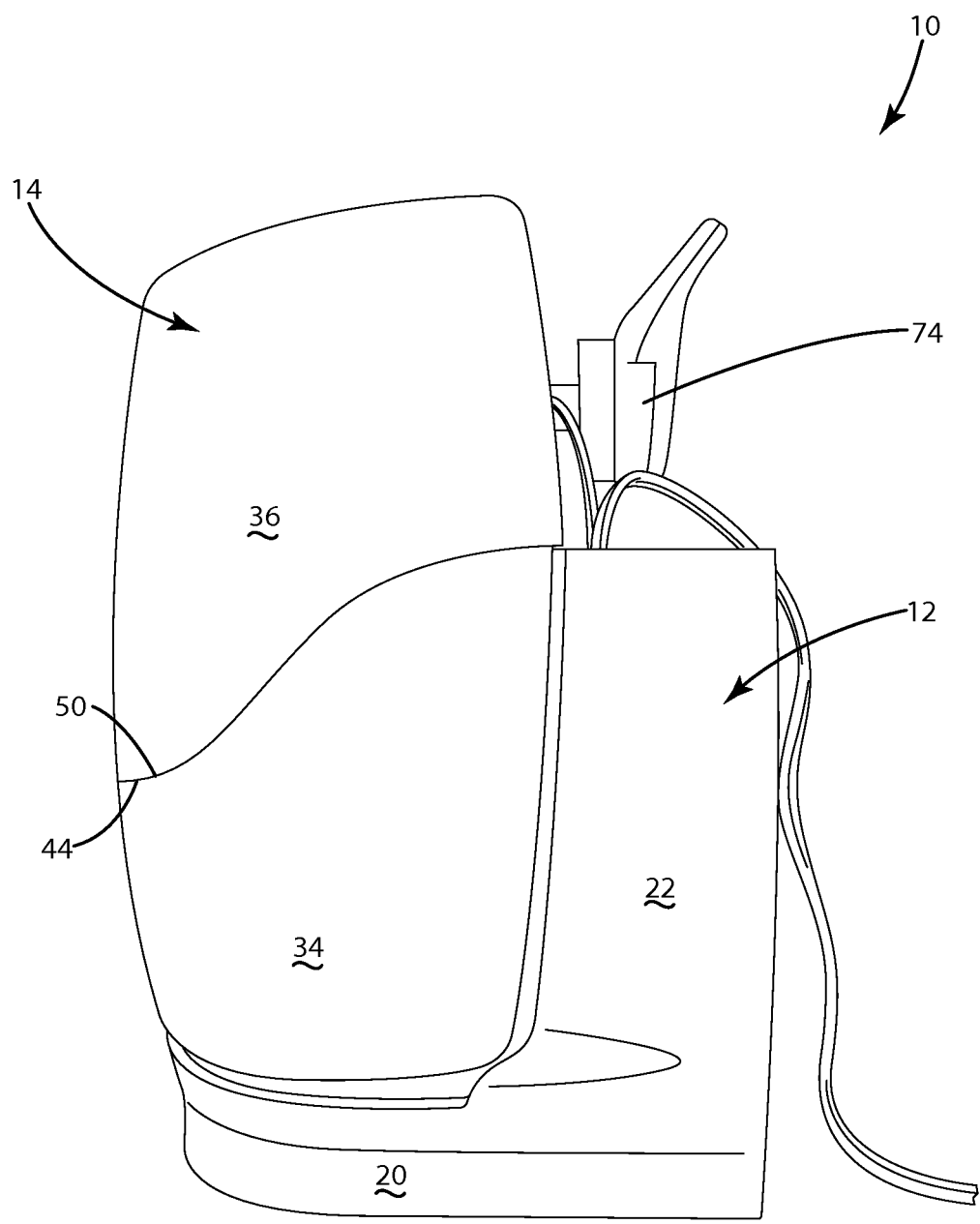
FIG. 1 is a side elevational view of a humidifier system.

The current embodiments relate to a system and a method for treating humidified air with germicidal radiation. The system generally includes a humidifier including an internal ultraviolet light source for treating atomized water and/or water vapor prior to its release into the surrounding environment. More specifically, and with reference to FIG. 1, an improved humidifier system is generally designated 10. The improved humidifier system 10 includes a base station 12 and a humidifier 14. As explained in greater detail below, the base station 12 is operable to provide a source of untreated, dry air to the humidifier 14, and the humidifier 14 is operable to humidify the dry air and to treat the resulting humidified air with germicidal radiation from an internal ultraviolet light source 16.

Figure 2:
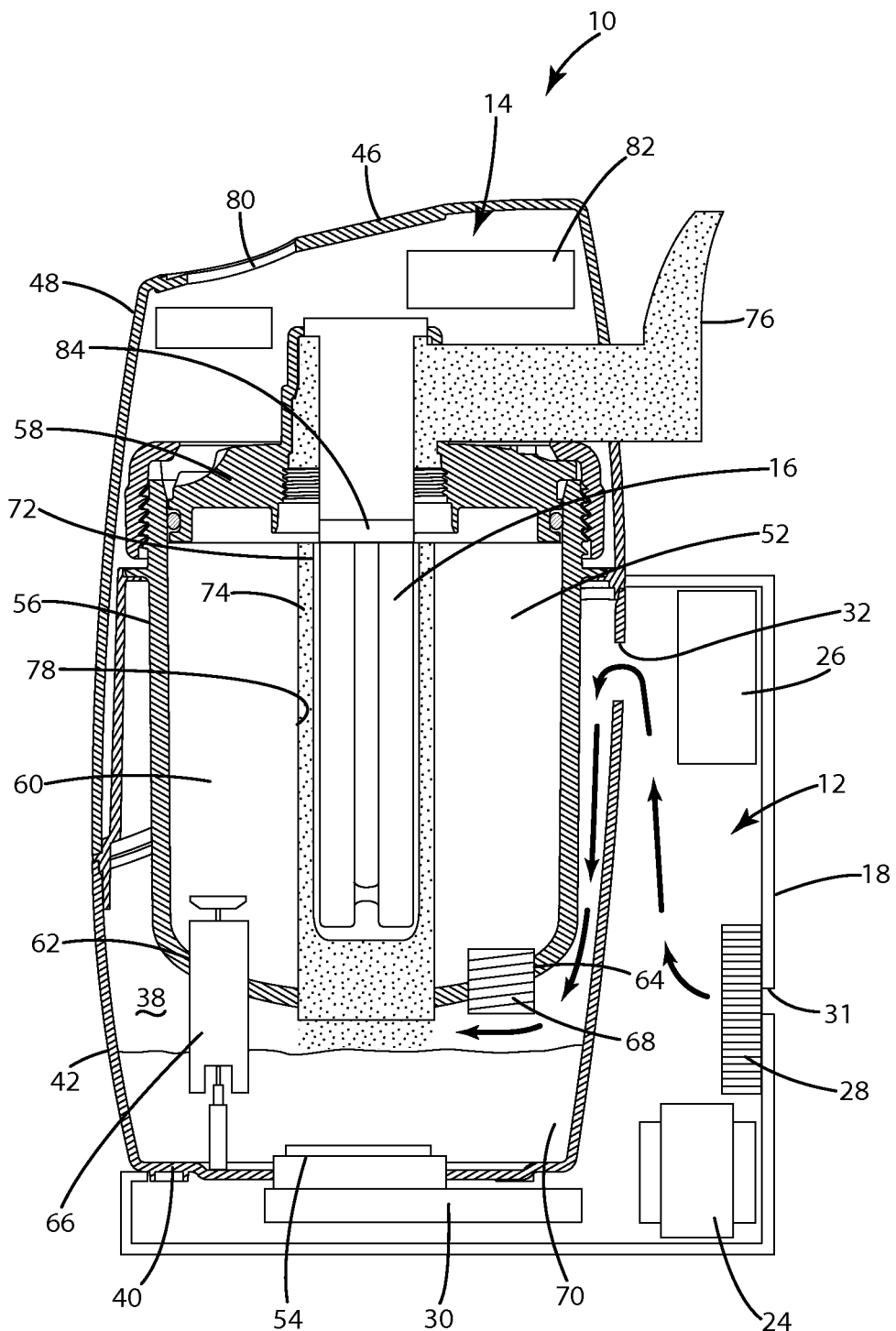
FIG. 2 is a cross sectional view of the humidifier system of FIG. 1.

Referring now to FIGS. 1-2, the base station 12 includes an outer housing 18 forming a seat 20 and a generally upright back portion 22. The housing 18 generally forms an enclosure for a transformer 24, a power adapter 26, a blower 28 and a nebulizer module 30. The transformer 24 is operable to convert a mains voltage into a stepped down voltage, and is electrically connected to the power adapter 26. The power adapter 26 provides a regulated DC or AC output to the blower 28, the nebulizer module 30 and the humidifier 14 according to their respective power consumption needs. The blower 28, optionally a motorized rotary fan, draws dry air into the base station 12 through an opening 31 in the housing 18. The general movement of air flow through the base station 12 is shown by the arrows in FIG. 2.

Referring again to FIG. 1, the humidifier 12 is removably seated with the base station 12 and includes a lower housing unit 34 and an upper housing unit 36. The lower housing unit 34 and the upper housing 36 cooperatively define a humidifier enclosure 38. Optionally, the lower housing unit 34 includes a base 40 and an upward extending sidewall 42 terminating in a first periphery 44. The first periphery 44 extends in an upwardly sloped manner from a forward portion of the humidifier 14 to a rearward portion of the humidifier 14. In corresponding fashion, the upper housing unit 36 can optionally include a cover 46 and a downwardly extending sidewall 48 terminating at a second periphery 50. The second periphery 50 extends in a downwardly sloped manner from the rearward portion of the humidifier 14 to the forward portion of the humidifier 14 to define a mating surface for cooperative engagement with the first periphery 44.

As noted above, the humidifier 14 is generally operable to humidify dry air from the base station 12 and to treat the resulting humidified air with germicidal radiation from the internal ultraviolet light source 16. As shown in FIG. 2, the humidifier 14 can also include a water reservoir 52 and a nebulizer 54 or other device for generating a mist of humidified air. The water reservoir 52 can include a reservoir body 56 to matably interfit with a reservoir cap 58. The reservoir body 56 and the reservoir cap 58 cooperate to define a toroidal space 60 having an interior diameter sized to receive the ultraviolet lamp 16, and an exterior diameter sized to fit within the humidifier housing 34. The reservoir body 56 can define a first opening 62 for a flow valve 66 and a second opening 64 for a fill cap 68. The lower housing unit 34 is generally configured to support the water reservoir 52 in the upside down position, where the fill plug 68 is at or near the lowermost portion of the water reservoir 52 when seated within the humidifier 14.

Water from the water reservoir 52 is selectively distributed into a nebulizing chamber 70 in a lowermost portion of the lower housing unit 34. The water reservoir 52 and the nebulizing chamber 70 are in fluid communication through the flow valve 66 for providing a metered flow of untreated water from the water reservoir 52 to the nebulizer chamber 70. Optionally, the nebulizer chamber 70 forms part of the base 40 and the sidewall 42 of the humidifier housing 34. Alternatively, the nebulizing chamber 70 can include a tray separate from the base 40 and the sidewall 42 which may be removed for cleaning. In both configurations, the nebulizing chamber 70 includes the nebulizer 54. The nebulizer 54 is operatively interfaced with the nebulizer module 30 in the base station 12. In use, the nebulizer 54 can humidify the air immediately above the water in the nebulizing chamber 70. For example, when water comes into contact with the nebulizer 54, ultrasonic vibrations cause the water to be broken up into small droplets which are propagated away from the nebulizer 54. The droplets evaporate to increase the humidity of the air in the nebulizing chamber 70. Air flow from an opening 32 in the rearward portion of the housing 14 assists in carrying the humidified air upwardly and away from the nebulizing chamber 70.

Referring again to FIG. 2, the humidifier 14 includes an ultraviolet light source 16 configured to impart germicidal radiation on all or a part of the escaping humidified air. In one embodiment, the ultraviolet light source 16 includes an ultraviolet lamp that emits ultraviolet light at one or more germicidal wavelengths. The ultraviolet lamp 16 is seated within a lamp sleeve 72 and within a cylindrical channel 74. Humidified air from beneath the ultraviolet lamp 16 is drawn through the channel 74, along the exterior of the lamp sleeve 72, and out through a discharge vent 76 in the upper housing unit 36. The lamp sleeve 72 can include a glass sleeve, crystal sleeve, or other material transmissive to ultraviolet light from the ultraviolet lamp 16. In addition, the cylindrical channel 74 can include an interior surface 78 substantially reflective of ultraviolet light. Alternatively, the cylindrical channel 74 can be substantially transmissive to ultraviolet light for treating water in the reservoir 52. In either configuration, unhumidified air is drawn into the nebulizing chamber 70 through the opening 32 in the humidifier housing 34. Once within the nebulizing chamber 70, the nebulizer 54 causes a portion of the water to atomize into a water vapor. The unhumidified air combines with the water vapor to become humidified air. The humidified air is then exposed to germicidal radiation from the ultraviolet light source 16 to break down any of various microorganisms that are or may be present in the water.

While the nebulizing chamber 70 is described above as including a nebulizer 54, the chamber 70 can include essentially any device for humidifying air. For example, the chamber 70 can include an evaporative wick-and-filter system common in many portable humidifiers. Alternatively, the chamber 70 can include a vaporizer, impeller systems or ultrasonic systems. In these embodiments, water molecules accumulate as water vapor in the nebulizing chamber 70. At least some of the water vapor is drawn upward from the nebulizing chamber 70 for germicidal treatment prior to discharge substantially as described above in connection with FIGS. 1-2.

In one embodiment, the humidifier 12 includes a control panel 80 to facilitate user selection of one or more humidifier settings. The control panel 80 can include one or more selection devices, such as a knob or a dial, to select a desired humidity level. For example, the selection device can be coupled to a humidistat to terminate power to the nebulizer 54 when the desired humidity level has been reached. In this configuration, the humidifier 14 shuts off when the ambient air reaches the desired humidity. Similarly, the humidifier 14 turns on if the ambient humidity drops below the desired humidity level. In addition, the humidifier 14 can include a control module 82 to regulate one or more of the various humidifier components. For example, the control module 82 can control operation of the blower 28 to regulate the flow of air through the base station 12 and the humidifier 14. In addition, the control module 82 can control operation of the nebulizer 54 to regulate the moisture content of the discharged air flow. In addition, the control module 82 can control operation of the ultraviolet light source 16 through a suitable ballast 84. The ballast 84 may include a wireless power supply or other device for wirelessly transferring power to the ultraviolet bulb 16. For example, the ballast 84 may include a resonance-seeking ballast circuit substantially as set forth in U.S. Pat. No. 6,825,620, entitled "Inductively Coupled Ballast Circuit," the disclosure of which is incorporated by reference in its entirety.

In some embodiments, the control module 82 can also monitor the operating parameters of the ultraviolet lamp 16. For example, the control module 82 can monitor the lamp power consumption during start-up and normal operation, the lamp luminary output during start-up and normal operation, and the overall duration of lamp operation. An optional RFID system can determine whether an existing lamp has been replaced with a new lamp. The control panel 80 can include a display, for example an LCD display, to relate such information to a user. The display can also indicate the remaining water level, the blower speed, the nebulizer rate, and other performance characteristics. For example, the control panel 80 can generate a visual or audible alert when the ultraviolet lamp 16 is performing outside of acceptable parameters. Still optionally, the control module 82 can include a lockout device to prevent the humidifier 14 from operating if the ultraviolet lamp 16 is not properly seated within the humidifier 14 or if the ultraviolet lamp 16 is not operating within acceptable parameters.

Figure 3:
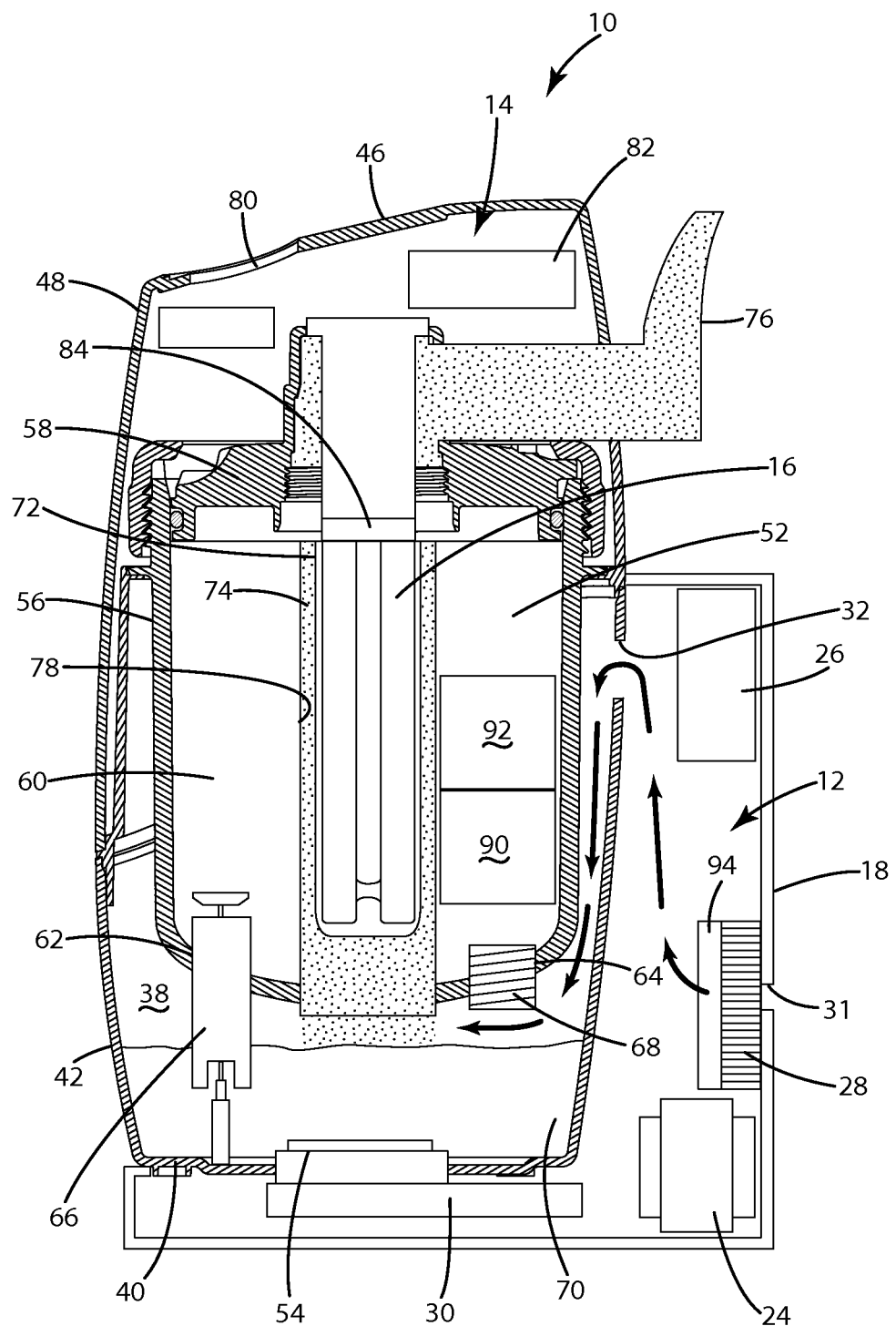
FIG. 3 is a cross sectional view of the humidifier system of FIG. 1 including a carbon cartridge and a hardness removing module.

In certain applications, it can be desirable to remove impurities from the water supply prior to humidifying the intake air, particularly where distilled water is not utilized. For example, it can be desirable to remove materials commonly found in hard water prior to atomization in the nebulizing chamber 70. As shown in FIG. 3, the reservoir 52 can optionally include a carbon cartridge filter 90 and a hardness removing module 92. A first mounting structure detachably secures the carbon cartridge 90 to the water reservoir 52. The carbon cartridge 90 can be positioned within the water reservoir 52 adjacent the fill plug 68 such that the carbon cartridge 90 is in fluid communication with the reservoir inlet 64. The carbon cartridge 90 can be configured to remove large suspended solids and other contaminants. For example, the carbon filter 90 can be configured to filter contaminants at a flow rate of 7.0 mL/min of water with a total capacity of approximately 100 liters per year. A second mounting structure detachably secures the hardness removing module 92 to the water reservoir 52. The hardness removing module 92 can be positioned within the water reservoir 52 in fluid communication between the carbon cartridge 90 and the flow valve 66. The hardness removing module 92 can be configured to remove chlorine and oxide metals from the water. For example, the hardness removing module 92 can be configured to remove chlorine, oxide metals and other minerals using suitable thin film distillation and/or reverse osmosis techniques. The carbon cartridge 90 and the hardness removing module 92 can be serially connected in a flow path from the reservoir inlet 64 to the reservoir outlet 62. The carbon cartridge 90 and hardness removing module 92 cooperate to reduce white dust precipitate from the humidified air, as well as preventing calcium buildup on the nebulizer. This is particularly desirable where the supply water is high in mineral deposits, such as with well water or unsoftened water. The humidifier 14 can also include a HEPA filter 94 in the air flow path to filter the untreated air or the humidified air. For example, a HEPA filter 94 can be positioned in the air flow path before or after the ultraviolet lamp 16. The remaining operational life of the carbon cartridge 90, the hardness removing module 92 and the HEPA filter 94 can also be indicated on the control panel display 80.

In combination with the embodiments described above, it may be desirable to provide power to the base station 12 and/or the humidifier 14 without the use of conventional electrical contacts. In certain applications it can also be desirable to reduce the exposure of certain components—for example the nebulizer module 30 and the ultraviolet bulb 16—to water and moisture to thereby reduce the risk of electric shock. In these applications, the humidifier system 10 can include an inductive power system such as disclosed in U.S. Pat. No. 6,825,620 entitled "Inductively Coupled Ballast Circuit," U.S. Pat. No. 7,212,414 entitled "Adaptive Inductive Power Supply," and U.S. Pat. No. 7,522,878 entitled "Adaptive Inductive Power Supply with Communication," the disclosures of which are incorporated by reference in their entirety.

While described above in connection with a system having a base station 12 and a humidifier 14, the system 10 may instead be self-contained within a single portable housing. Such a self-contained system 10 can be conveniently employed wherever humidification is desired. Where a base station 12 and humidifier 14 are utilized, the above noted base station systems can instead pertain to the humidifier 14, and the above noted humidifier systems can instead pertain to the base station 12. In addition, the humidifier system 10 can be incorporated into any of a variety of forced-air humidifier systems. This can include drum style forced-air humidifiers, disc wheel style humidifiers, bypass flow-through style humidifiers, and spray mist forced air humidifiers, for example.

The above descriptions are those of the current embodiments of the invention. Various alterations and changes can be made without departing from the spirit and broader aspects of the invention as defined in the appended claims, which are to be interpreted in accordance with the principles of patent law including the doctrine of equivalents. Any reference to elements in the singular, for example, using the articles "a," "an," "the," or "said," is not to be construed as limiting the element to the singular.

The invention claimed is:

1. A humidifier system comprising:
 a humidifier housing defining an air inlet, and air outlet, and a fluid flow path therebetween, the fluid flow path being adapted to direct air through the humidifier housing;
 an atomizing chamber at a first portion of the fluid flow path, the atomizing chamber being adapted to increase the moisture content of a volume of air circulating through the fluid flow path;
 an ultraviolet light source at a second portion of the fluid flow path, the ultraviolet light source being adapted to expose the volume of humidified air from the atomizing chamber with germicidal light prior to its release from the humidifier housing at the air outlet; and
 a base station having a blower to draw ambient air into the humidifier housing.

2. The humidifier system of claim 1 wherein the atomizing chamber includes one of an ultrasonic nebulizer, a wick filter, and a steam vaporizer.

3. The humidifier system of claim 1 wherein the fluid flow path includes a sidewall spaced apart from the ultraviolet light source.

4. The humidifier system of claim 3 wherein the sidewall is substantially cylindrical.

5. The humidifier system of claim 1 further including a water reservoir in fluid communication with the atomizing chamber.

6. The humidifier system of claim 5 wherein the water reservoir includes at least one of a carbon cartridge filter and a hardness removing module.

7. A method for humidifying air, comprising:
providing a fluid flow path in communication with the ambient environment, the fluid flow path including an inlet, an atomizing chamber, an ultraviolet light source, and an outlet;
increasing the moisture content of ambient air circulating through the atomizing chamber in the fluid flow path;

exposing the resulting humidified air escaping from the atomizing chamber with ultraviolet light from the ultraviolet light source to inactivate microorganisms in the humidified air, the ultraviolet light source being in the fluid flow path downstream of the atomizing chamber; and discharging the humidified air from the fluid flow path outlet and into the ambient environment, wherein the increased moisture content originates from a water supply within a water reservoir, and wherein the water reservoir defines a toroidal core, the fluid flow path extending vertically through the toroidal core.

8. The method according to claim 7 wherein increasing the moisture content includes introducing atomized water into the fluid flow path.

9. The method according to claim 7 further including filtering ambient air circulating through the fluid flow path.

10. The method according to claim 7 wherein the fluid flow path is partially defined by a cylindrical sidewall spaced apart from an ultraviolet light source.

11. The method according to claim 7 wherein the water reservoir includes at least one of a carbon cartridge filter and a hardness removing module.

12. A humidifier system comprising:

a humidifier housing defining an air inlet, and air outlet, and a fluid flow path therebetween, the fluid flow path being adapted to direct air through the humidifier housing;

a water reservoir within the humidifier housing and including a water reservoir outlet;

an atomizing chamber in fluid communication with the water reservoir outlet, the atomizing chamber being adapted to atomize water from the water reservoir to humidify ambient air circulating through the fluid flow path; and an ultraviolet light source adapted to treat the humidified air escaping from the atomizing chamber with germicidal radiation prior to its dispersal into the ambient environment, wherein the atomizing chamber is at a first portion of the fluid flow path and wherein the ultraviolet light source is at a second portion of the fluid flow path, and wherein the water reservoir defines a toroidal core, the ultraviolet light source extending vertically through the toroidal core.

13. The humidifier system of claim 12 further wherein the ultraviolet light source is housed within a channel including a sidewall spaced apart from the ultraviolet light source for defining a fluid flow path therebetween.

14. The humidifier system of claim 13 wherein the channel is cylindrical and includes an inner surface substantially reflective of ultraviolet light.

15. The humidifier system of claim 13 wherein the ultraviolet light source is oriented substantially vertically within the channel.

16. The humidifier system of claim 12 wherein the atomizing chamber includes one of an ultrasonic nebulizer, a wick filter, and a steam vaporizer.

17. The humidifier system of claim 12 wherein the water reservoir includes at least one of a carbon cartridge filter and a hardness removing module.

18. A humidifier system comprising:

a humidifier housing defining an air inlet, and air outlet, and a fluid flow path therebetween, the fluid flow path being adapted to direct air through the humidifier housing;

an atomizing chamber at a first portion of the fluid flow path, the atomizing chamber being adapted to increase the moisture content of a volume of air circulating through the fluid flow path;

an ultraviolet light source at a second portion of the fluid flow path, the ultraviolet light source being adapted to expose the volume of humidified air from the atomizing chamber with germicidal light prior to its release from the humidifier housing at the air outlet; and a fluid reservoir in fluid communication with the atomizing chamber, wherein the fluid reservoir defines a toroidal core, the fluid flow path extending upwardly through the toroidal core and including the ultraviolet light source at least partially therein.

* * * * *